(12) United States Patent
Karlsson

(10) Patent No.: US 9,775,750 B2
(45) Date of Patent: Oct. 3, 2017

(54) SIGNAL LAYER FOR AN ABSORBENT ARTICLE

(75) Inventor: Elisabeth Karlsson, Kungsbacka (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 568 days.

(21) Appl. No.: 14/362,929

(22) PCT Filed: Dec. 9, 2011

(86) PCT No.: PCT/SE2011/051497
§ 371 (c)(1),
(2), (4) Date: Jun. 5, 2014

(87) PCT Pub. No.: WO2013/085447
PCT Pub. Date: Jun. 13, 2013

(65) Prior Publication Data
US 2014/0303581 A1    Oct. 9, 2014

(51) Int. Cl.
*A61F 13/15*    (2006.01)
*A61F 13/42*    (2006.01)
(Continued)

(52) U.S. Cl.
CPC .............. *A61F 13/42* (2013.01); *A61F 5/455* (2013.01); *A61F 13/472* (2013.01);
(Continued)

(58) Field of Classification Search
CPC .......... A61F 13/00055; A61F 13/00059; A61F 13/42; A61F 13/4756; A61F 13/512;
(Continued)

(56) References Cited

U.S. PATENT DOCUMENTS 3,918,454 A * 11/1975 Korodi .................... A61F 13/42
604/361
4,738,674 A *  4/1988 Todd ....................... A61F 5/485
5/484
(Continued)

FOREIGN PATENT DOCUMENTS

CA    2555829 A1    6/1999
CN    1143902 A    2/1997
(Continued)

OTHER PUBLICATIONS

Extended European Search Report dated Aug. 4, 2015, issued in corresponding European Patent Application No. 11877099.9 (6 pages).
(Continued)

*Primary Examiner* — Jacqueline Stephens
(74) *Attorney, Agent, or Firm* — Drinker Biddle & Reath LLP

(57) ABSTRACT

A signal layer for an absorbent article provided to absorb menstrual fluid includes a pattern of capillary channels allowing capillary action such that discharged menstrual fluid that comes across one of the openings in the capillary channels enters into the capillary channels and is retained therein due to the capillary force. The color of the retained menstrual discharge dyes or colors the pattern for signaling purpose, and the pattern is directly or indirectly visible to an observer.

20 Claims, 15 Drawing Sheets

(51) Int. Cl.

| | |
|---|---|
| *A61F 5/455* | (2006.01) |
| *A61F 13/472* | (2006.01) |
| *A61F 13/475* | (2006.01) |
| *A61F 13/512* | (2006.01) |
| *A61F 13/537* | (2006.01) |
| A61F 13/00 | (2006.01) |
| A61F 13/84 | (2006.01) |

(52) U.S. Cl.
CPC ........ *A61F 13/4756* (2013.01); *A61F 13/512* (2013.01); *A61F 13/5376* (2013.01); *A61F 13/00055* (2013.01); *A61F 13/00059* (2013.01); *A61F 2013/422* (2013.01); *A61F 2013/53778* (2013.01); *A61F 2013/53782* (2013.01); *A61F 2013/8497* (2013.01)

(58) Field of Classification Search
CPC ............ A61F 13/5376; A61F 2013/422; A61F 2013/53778
USPC .................................................. 604/361, 359
See application file for complete search history.

(56) References Cited

U.S. PATENT DOCUMENTS

| | | | |
|---|---|---|---|
| 5,401,267 | A | 3/1995 | Couture-Dorschner et al. |
| 5,647,863 | A | 7/1997 | Hammons et al. |
| 6,171,291 | B1 | 1/2001 | Osborn, III et al. |
| 7,867,210 | B2 | 1/2011 | Mori et al. |
| 2002/0133132 | A1 | 9/2002 | Copat et al. |
| 2003/0135174 | A1 | 7/2003 | Benecke et al. |
| 2004/0127875 | A1 | 7/2004 | Hammons et al. |
| 2006/0142710 | A1 | 6/2006 | Kigata et al. |
| 2006/0224132 | A1 | 10/2006 | Roe et al. |
| 2008/0132864 | A1 | 6/2008 | Lawson et al. |

FOREIGN PATENT DOCUMENTS

| | | |
|---|---|---|
| CN | 201005873 Y | 1/2008 |
| CN | 101151008 A | 3/2008 |
| EP | 2184041 A2 | 5/2010 |
| GB | 2258840 B | 4/1995 |
| JP | 2004-236826 A | 8/2004 |
| JP | 2006-26081 A | 2/2006 |
| RU | 2221529 C2 | 1/2004 |
| RU | 2222300 C2 | 1/2004 |
| RU | 2232605 C2 | 7/2004 |
| RU | 2387430 C2 | 4/2010 |
| WO | WO-91/19471 A1 | 12/1991 |
| WO | WO 95/24877 A1 | 9/1995 |
| WO | WO 00/35503 | 6/2000 |
| WO | WO 00/62729 | 10/2000 |
| WO | WO 2006/110502 A1 | 10/2006 |
| WO | WO-2009/001711 A1 | 12/2008 |

OTHER PUBLICATIONS

English language translation of a Chinese Office Action dated Feb. 22, 2016 issued in corresponding Chinese patent application No. 201180074693.3 (8 pages).
Russian Decision on Grant dated Dec. 11, 2015 issued in corresponding Russian patent application No. 2014127893 (8 pages) (with 5 pages English translation).
Examination Report dated Jul. 27, 2015 issued in corresponding Mexican Patent Application No. MX/a/2014/006707 and its English language translation (7 pages).
Examination Report dated Aug. 11, 2015 issued in corresponding Russian Patent Application No. 2014127893 and its English language translation (6 pages).
Australian Patent Examination Report No. 1 dated Aug. 22, 2014, issued in corresponding Australian patent application No. 2011382661 (4 pages).
Decision on Rejection issued on Mar. 15, 2017 in Chinese Patent Application No. 201180074693.3 (9 pages) with an English translation (9 pages).

* cited by examiner

SIGNAL LAYER FOR AN ABSORBENT ARTICLE

CROSS-REFERENCE TO PRIOR APPLICATION

This application is a §371 National Stage Application of PCT International Application No. PCT/SE2011/051497 filed Dec. 9, 2011, which is incorporated herein in its entirety.

TECHNICAL FIELD

The disclosure relates to a signal layer for an absorbent article provided to absorb menstrual fluid.

BACKGROUND

Layers forming absorbent articles having different characteristics are well known in the art. An absorbent article may for instance be made up by an upper layer, a distribution layer, an acquisition layer, different kinds of absorbent bodies and a back sheet.

However, the development of absorbent articles has lead to an increased capability of hiding discharged fluid beneath the top layer such that it may not always be visible after use. This may lead to a used article that may look unused or an insecurity may arise whether or not an article actually has been used.

There exists a need for a solution to the above mentioned problem.

SUMMARY

It is desired to provide a signal layer for an absorbent article provided to absorb menstrual fluid where the previously mentioned problems are avoided. This can be achieved by a signal layer includes a pattern of capillary channels for allowing capillary action such that discharged menstrual fluids that comes across one of the openings in the capillary channels enters into the capillary channels and are retained therein due to the capillary force, wherein the colour of the retained menstrual discharge dyes/colours the pattern for signalling purpose and wherein the pattern is directly or indirectly visible for an observer.

The disclosure relates to a signal layer for an absorbent article provided to absorb menstrual fluid. The signal layer includes a pattern of capillary channels for allowing capillary action such that discharged menstrual fluids that comes across one of the openings in the capillary channels enters into the capillary channels and are retained therein due to the capillary force. The colour of the retained menstrual discharge dyes/colours the pattern for signalling purpose. The pattern is directly or indirectly visible for an observer. That the pattern is directly visible means that the signal layer can be positioned such that the signal layer is located as an outermost layer of the absorbent article or that the signal layer is located beneath a transparent outermost layer. Indirectly visible means that the signal layer is positioned such that the signal layer is located beneath an outermost layer that is translucent enabling the signal layer to be visible through the layer while the signal layer at the same time is somewhat obscured by the outermost layer. Thus, the signal layer does not have to be visible before use but may be placed beneath a translucent layer such that the signal layer is only visible when dyed.

One advantage of having a signal layer as disclosed is that a user easily can see how much of the product has been utilised. The capillary channels absorb small quantities of menstrual fluid thereby giving rise to a colouring or dying of the signal layer.

The signal layer is visible from at least one direction of the absorbent article, i.e. at least from a side facing the wearer during use or a side facing away from the wearer during use.

The signal layer may be positioned in the absorbent article such that it is visible through a back sheet in the absorbent article. Having a signal layer positioned such that it is visible through a back sheet after the menstrual discharge has entered into the capillary channels makes it possible to detect if there has been any leaks from the sides down through the back sheet.

The signal layer may be an upper layer in the absorbent article.

The signal layer may be positioned in the absorbent article such that it is visible through an upper layer in the absorbent article.

The signal layer may be a distribution layer and/or an acquisition layer.

The signal layer may include any layer of the absorbent article depending on the desired effect of the signal layer. It is also possible for an absorbent article to include more than one signal layer, for instance one signal layer positioned near the top part of the absorbent article and one signal layer positioned near the bottom part of the absorbent article.

The upper layer includes through openings for allowing menstrual fluids to pass through the upper layer.

The through openings allow the menstrual fluid to pass through the upper layer into the absorbent article for instance to an absorption body where it is stored or to a distribution layer and/or an acquisition layer.

The signal layer may include through openings for allowing menstrual fluids to pass through the signal layer.

The through openings allow the menstrual fluid to pass through the signal layer into the absorbent article for instance to an absorption body where it is stored or to a distribution layer and/or an acquisition layer.

The through openings may be slits, bent openings, angled through openings, maze like through openings, for at least partly hindering menstrual fluids to be visible through the through openings.

By having through openings that at least partly hinders menstrual fluid to be visible through the through openings the effect of the signal layer becomes more efficient as the signal layer will be the most distinguishable layer in the article.

The upper layer may have a thickness equal to or larger than the extent of the capillary channels through opening. This is to reduce the contact area between the upper layer and underlying layers. The capillary channels may have a length that is equal to or larger than the width of a capillary channel through opening. The underlying layers can in some cases be absorbent and may, if the contact area is too great, drain fluid from the capillary channels, thereby emptying them. The capillary channels and the through openings are made by pushing material down into the layer using for instance needles or other known techniques. This creates downward facing walls of the capillary channels and the through openings. The length of the capillary channels may be shorter than the length of the through openings and thus the layer that the through openings are positioned in. This ensures that the capillary channels to a lesser extent or not at all come in contact with the underlying layers. This avoids the capillary channels to be drained by that fluid is pulled from the capillary channels to an underlying layer.

The upper layer may be a laminate including non-woven bound to a substrate, which non-woven is subtle to a user and translucent and/or transparent. The use of non-woven layer enables the absorbent article to have a soft surface which is comfortable to the user while still allowing the layer or layers below to be directly or indirectly visible.

The signal layer may be a laminate including non-woven bound to the signal layer, which non-woven is subtle to a user and translucent and/or transparent. The use of a non-woven layer enables the absorbent article to have a soft surface which is comfortable to the user while still allowing the layer or layers below to be directly or indirectly visible in case the signal layer is placed directly beneath.

The signal layer may be made from a plastic film being perforated.

The signal layer may be a laminate of several layers. In some embodiments, the capillary channels are formed such that they extend through at least one of the layers making up the laminate such that the capillary channels come in contact with the menstrual fluid. The capillary channels may also extend through the entire laminate.

The capillary channels may be positioned in the striking zone.

The capillary channels may be positioned in the barrier zone for detection of a full article. This is to indicate that menstrual fluid has saturated the absorbent article.

The absorbent article may include an upper layer and back sheet opposing the upper layer, the absorbent article being delimited by two opposing and longitudinally extending longitudinal side edges and two opposing and laterally extending lateral side edges, the upper layer being directly or indirectly attached to the back sheet at least along the side edges.

The pattern of capillary channels described above may be designed to give an aesthetically appealing pattern such as for instance floral designs, pleasant abstract designs, heart shapes or other patterns that may give a positive experience for a user. Different designs may be combined to provide specific patterns. The designs may be combined with embossing, applications or ornamentations known in the art.

DETAILED DESCRIPTION OF DRAWINGS

Figure 1:
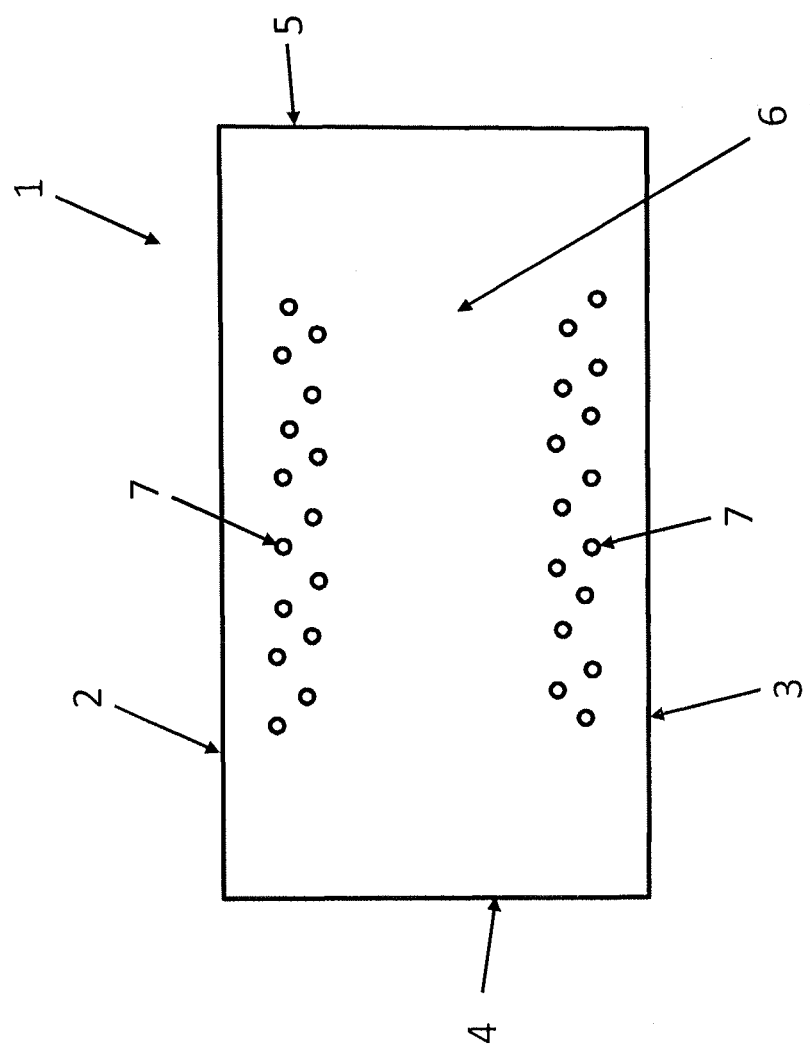
FIG. 1 schematically shows a signal layer according to a first embodiment.

FIG. 1 schematically shows a signal layer 1 according to a first embodiment. The signal layer 1 includes a first longitudinal side 2, a second longitudinal side 3, a first transverse side 4 and a second transverse side 5. The signal layer 1 includes a pattern 6 of capillary channels 7 extending at least partly through the signal layer 1. The capillary channels 7 are, in FIG. 1, positioned in a longitudinal pattern along the first longitudinal side 2 and the second longitudinal side 3 of the signal layer 1. The pattern 6 shown in FIG. 1 is intended as an example. Further examples of patterns 6 will be shown below. The signal layer 1 is made of, for instance, a perforated plastic film, perforated foam or a perforated non-woven. The signal layer 1 may also be laminated to, for instance, a non-woven layer. The capillary channels 7 may have dimensions (such as length and width) that are in the range of 0.06-0.08 cm. Depending on the design of the signal layer 1, the capillary channels 7 may have different lengths and widths. The relation between length and width may also be adapted for different designs of the signal layer 1.

Figure 2:
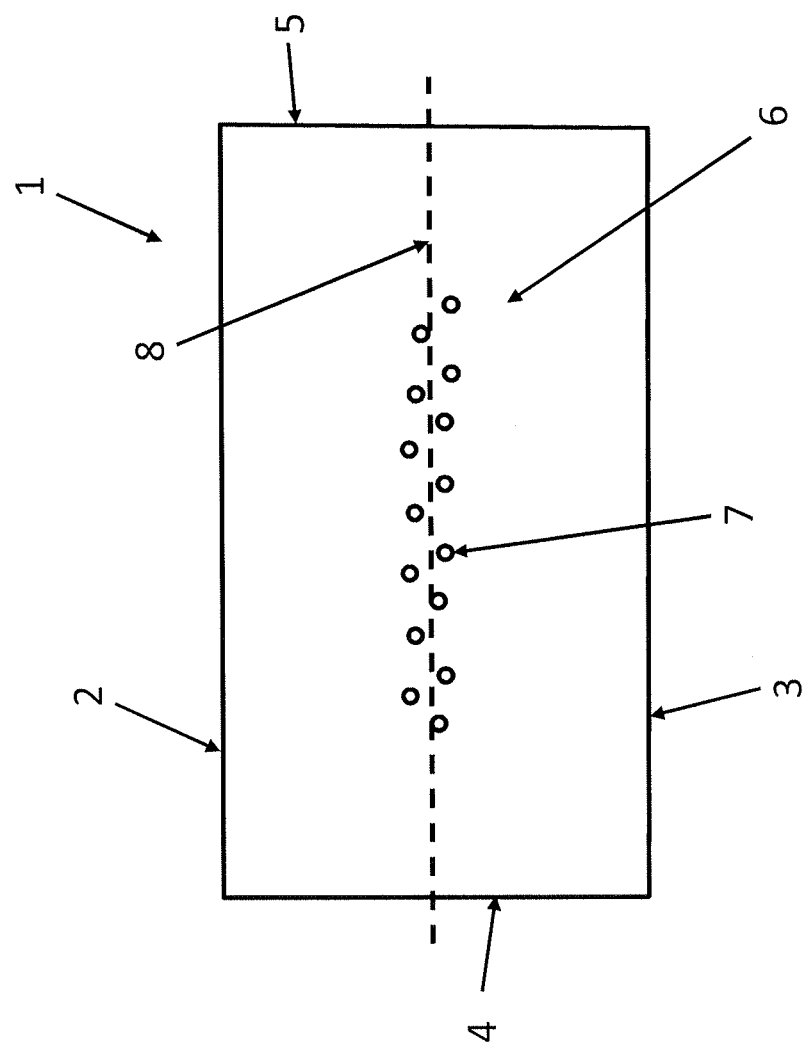
FIG. 2 schematically shows a signal layer according to a second embodiment.

FIG. 2 schematically shows a signal layer 1 according to a second embodiment. In FIG. 2, the capillary channels 7 are positioned in a longitudinal pattern 6 that is located essentially along a longitudinal central axis 8 of the signal layer 1.

Figure 3:
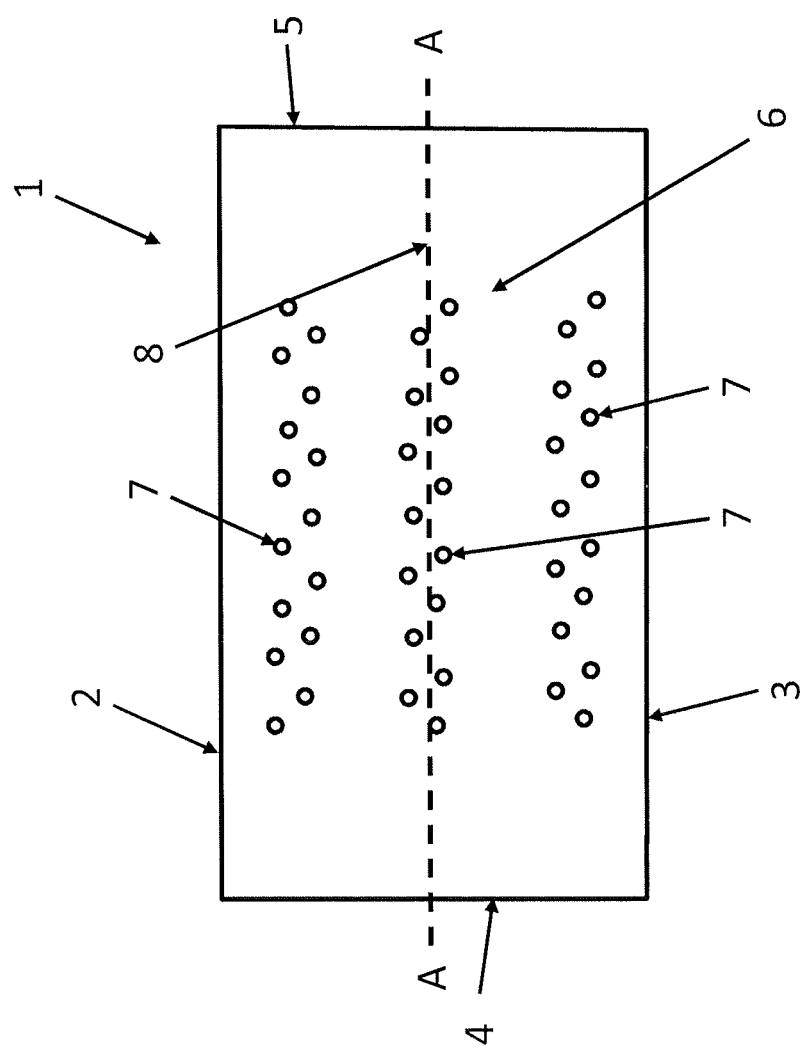
FIG. 3 schematically shows a signal layer according to a third embodiment.

FIG. 3 schematically shows a signal layer 1 according to a third embodiment. Here the pattern 6 of capillary channels 7 is a combination of the patterns shown in FIGS. 1 and 2. It is of course possible to have patterns that are positioned along the transverse sides 4, 5 and along a transverse central axis (not shown) of the signal layer 1. It is also possible to have the capillary channels 7 positioned more randomly than is shown in FIGS. 1-3.

Figure 4:
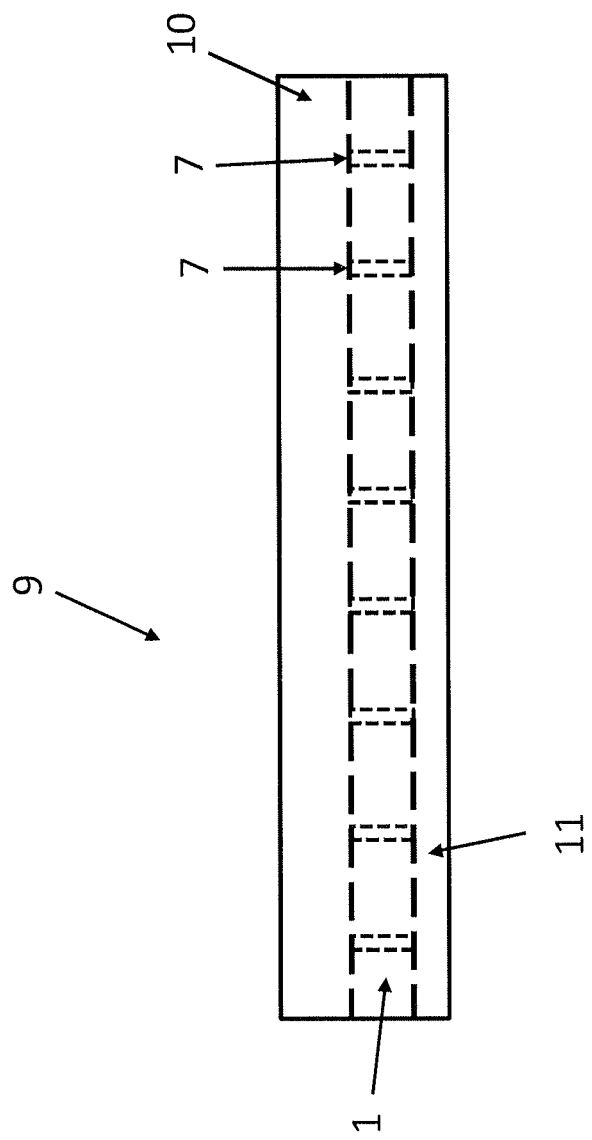
FIG. 4 schematically shows a side view of an absorbent article including a signal layer according to a fourth embodiment.

FIG. 4 schematically shows a side view of an absorbent article 9 including a signal layer 1 according to a fourth embodiment. The absorbent article 9 of FIG. 1 includes a signal layer 1 sandwiched between an upper layer 10 and a back sheet 11. The upper layer 10 may be made of non-woven or a non-woven bound to a substrate. The back sheet 11 may be made of a breathable or non-breathable film or a film/nonwoven material or a nonwoven material. In FIG. 4, the relative sizes of the upper layer 10, back sheet 11 and the signal layer 1 are merely illustrative. In FIG. 4, the capillary channels 7 in the signal layer 1 are evenly distributed along the length of the signal layer 1. The capillary channels 7 may also be located mainly in a zone corresponding to a striking zone of the absorbent article 9, i.e. the zone of the absorbent article 9 which is first contacted by the menstrual discharge. The striking zone may be a forward section or a rear section of the absorbent article 9 or a central section of the absorbent article 9. This is valid for any of the embodiments.

The absorbent article 9 is delimited by two opposing and longitudinally extending longitudinal side edges (not shown) and two opposing and laterally extending lateral side edges (not shown), the upper layer 10 being directly or indirectly attached to the back sheet 11 at least along the side edges.

Figure 5:
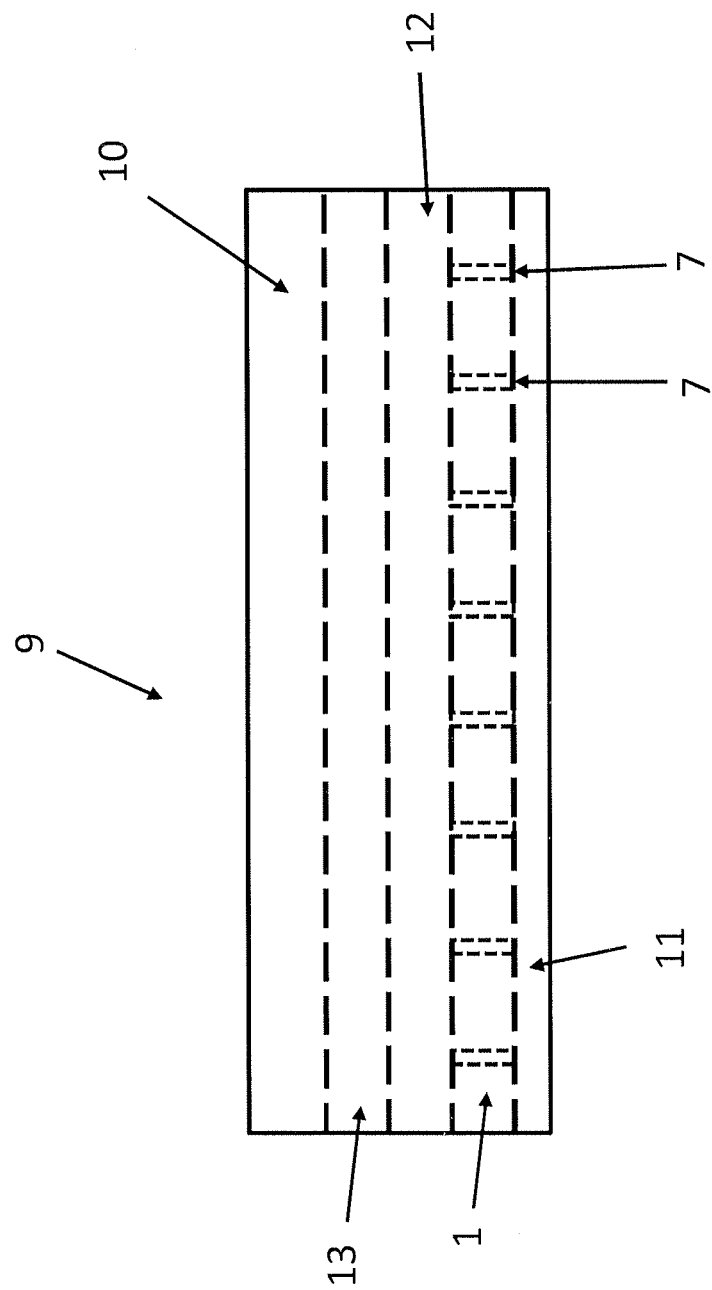
FIG. 5 schematically shows a side view of an absorbent article including a signal layer according to a fifth embodiment.

FIG. 5 schematically shows a side view of an absorbent article 9 including a signal layer 1 according to a fifth embodiment. In FIG. 5, the absorbent article 9 includes a signal layer 1 sandwiched between a back sheet 11 and an acquisition layer 12 of the absorbent article 9. The absorbent article 9 further includes an upper layer 10 and a distribution layer 13 located above the acquisition layer 12. Typical examples of an acquisition layer are layers made of different pulp compositions, pulp and superabsorbent particles or a mixture of pulp and synthetic fibres. Any combination of the above is of course possible. Typical examples of a distribution layer are tissue, air laid, high loft, foam or spunlace.

Figure 6:
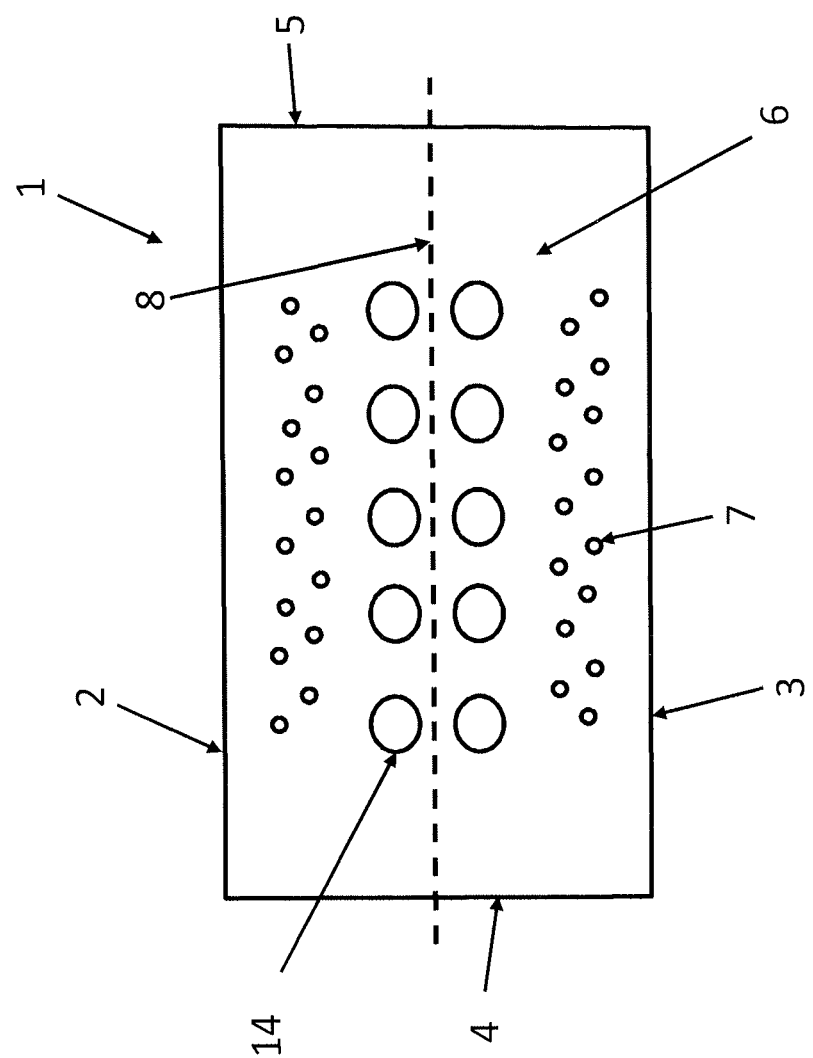
FIG. 6 schematically shows a signal layer according to a embodiment.
Figure 7:
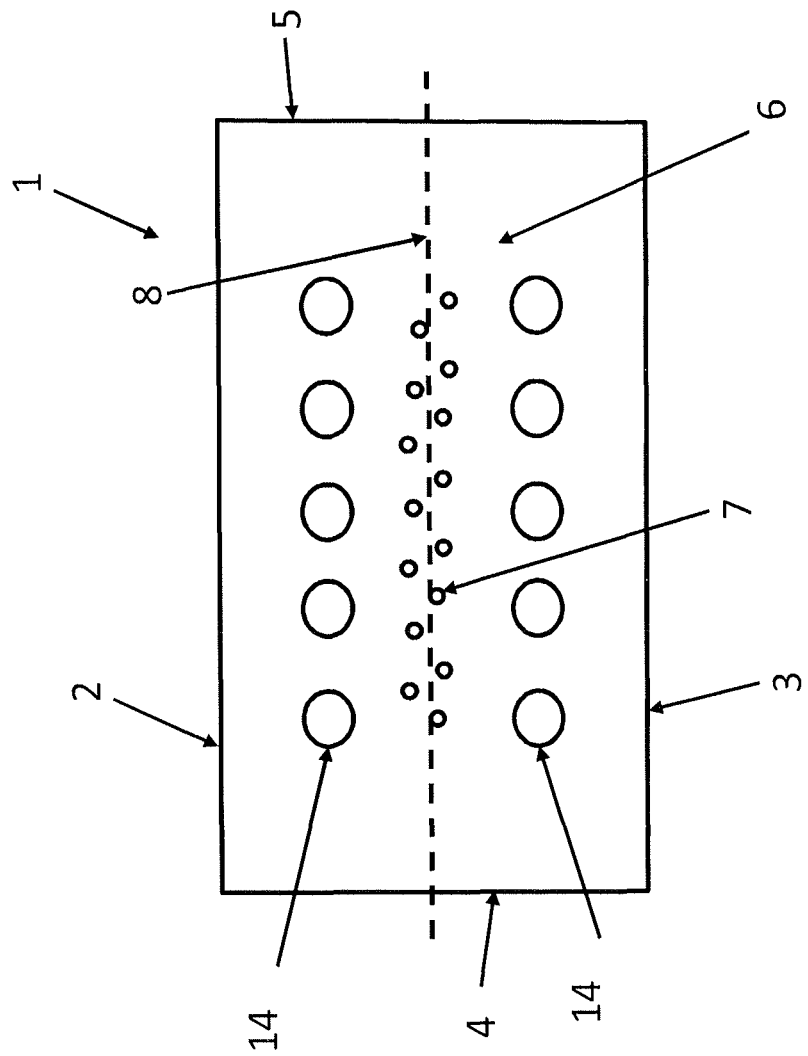
FIG. 7 schematically shows a signal layer according to a seventh embodiment.
Figure 8:
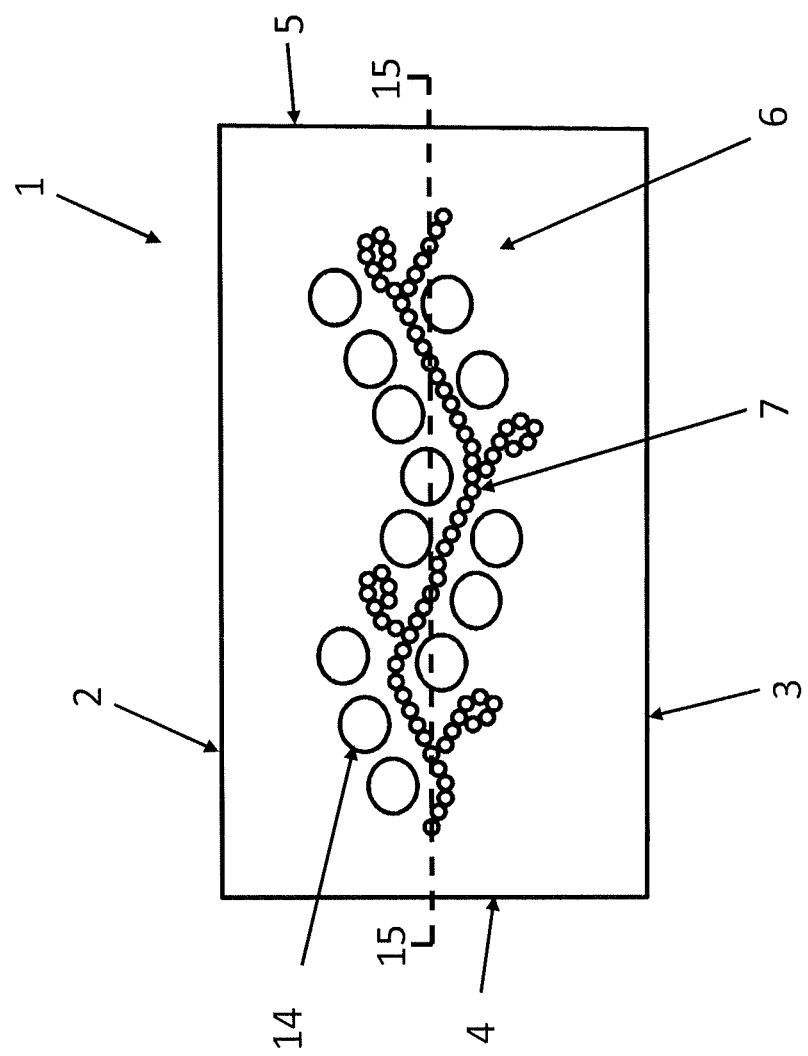
FIG. 8 schematically shows a signal layer according to an eighth embodiment.

FIGS. 6 to 8 schematically shows a signal layer 1 according to a sixth, seventh and eighth embodiment, respectively. In FIGS. 6 to 8, the signal layer 1 further includes through openings 14 besides the pattern 6 of capillary channels 7. The through openings 14 may be positioned centrally essentially along a longitudinal central axis 8 with the capillary channels 7 positioned along the longitudinal edges 2, 3 as is shown in FIG. 6. In FIG. 7, the through openings 14 are positioned along the longitudinal edges 2, 3 and the capillary channels 7 are positioned centrally essentially along a longitudinal central axis 8. FIG. 8 shows a signal layer 1 where the through openings 14 and the capillary channels 7 are positioned together forming a combined pattern 6 of through openings 14 and capillary channels 7, in this case a floral design. The positions of the through openings 14 and the capillary channels 7 described in conjunction with FIG. 6-8 may also be transversely oriented in the same way as is described in conjunction with FIGS. 1-3. The through openings 14 may have dimensions (such as length and width) that are in the range of 0.05-0.30 cm. Depending on the design of the absorbent article 9, the through openings 14 may have different lengths and widths. The relation between length and width may also be adapted for different designs of the absorbent article 9.

Figure 9:
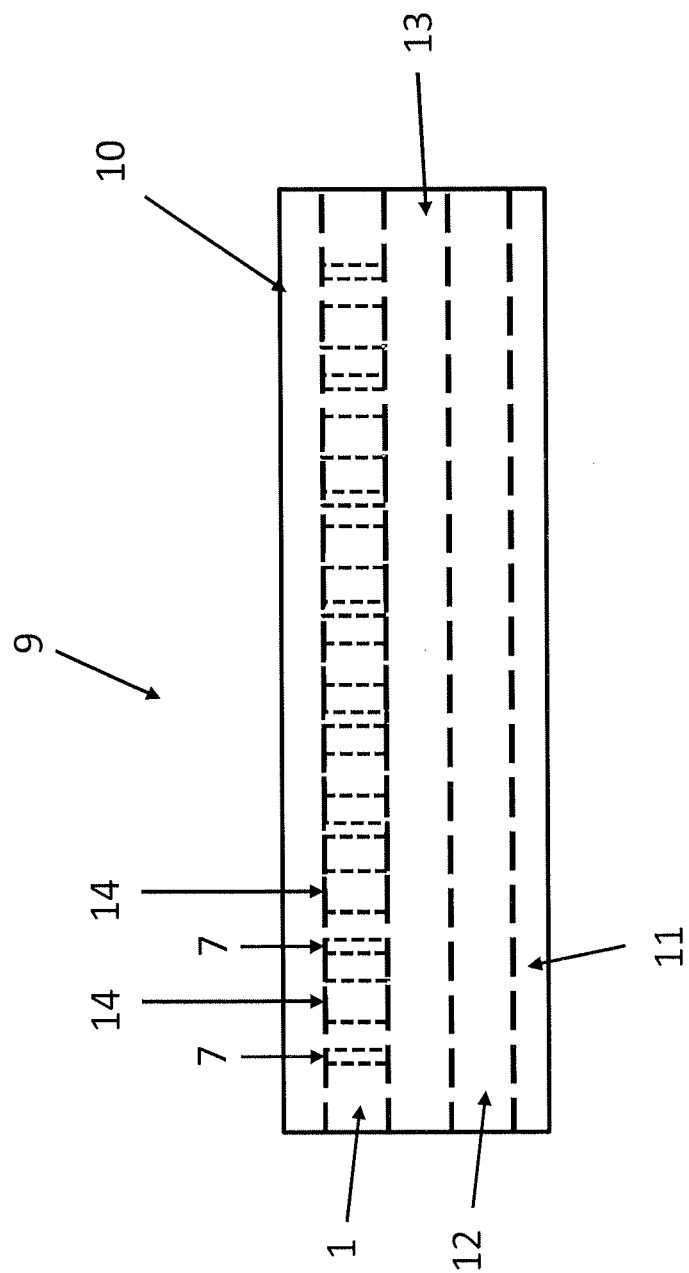
FIG. 9 schematically shows a side view of an absorbent article including a signal layer according to a ninth embodiment.

FIG. 9 schematically shows a side view of an absorbent article 9 including a signal layer 1 according to a ninth embodiment. Here a signal layer 1 according to any of FIGS. 6-8 is incorporated into an absorbent article 9. The absorbent article 9 may further include an upper layer 10, a distribution layer 13, an acquisition layer 12 and a back sheet 11. The upper layer 10, distribution layer 13, acquisition layer 12 and back sheet 11 are as described above. The distribution of through openings 14 and capillary channels 7 in FIG. 9 is merely intended as an illustration. The distribution of through openings 14 and capillary channels 7 will change depending on which of the aspects shown in FIGS. 6-8 that is used. This reasoning applies to all herein described absorbent products having both through openings and capillary channels.

Figure 10:
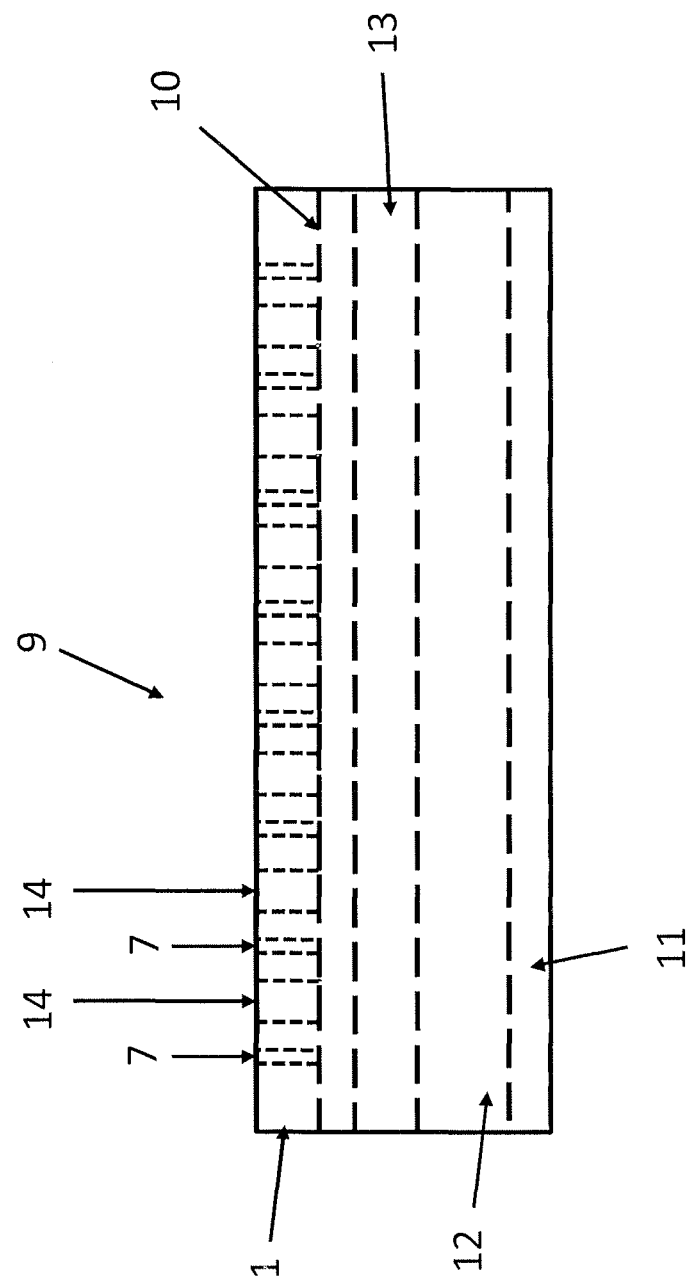
FIG. 10 schematically shows a side view of an absorbent article including a signal layer according to a tenth embodiment.

FIG. 10 schematically shows a side view of an absorbent article 9 including a signal layer 1 according to a tenth embodiment. The upper layer 10 of the absorbent article 9 is made up of a laminate of the signal layer 1 and an additional material.

Figure 11:
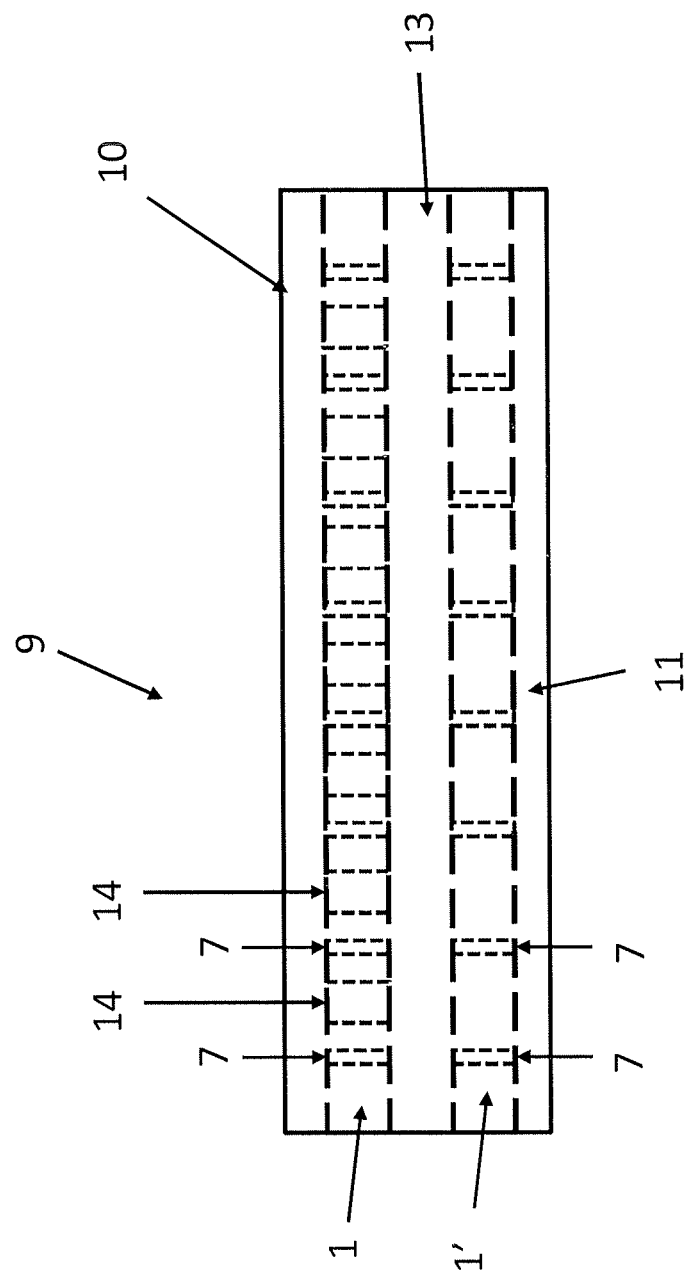
FIG. 11 schematically shows a side view of an absorbent article including a signal layer according to an eleventh embodiment.

FIG. 11 schematically shows a side view of an absorbent article 9 including a signal layer 1 according to an eleventh embodiment. In FIG. 11, the absorbent article 9 includes two signal layers (1, 1'). The first signal layer 1 is located below the upper layer 10 and may include a distribution layer 13.

The second signal layer (1') is located above the back sheet 11 or in a barrier zone for indicating a saturated article or a leak through any side edges. The barrier zone is the zone located near the back sheet 11 that is intended to form a barrier between the absorbent product and the underwear of a user.

Figure 12:
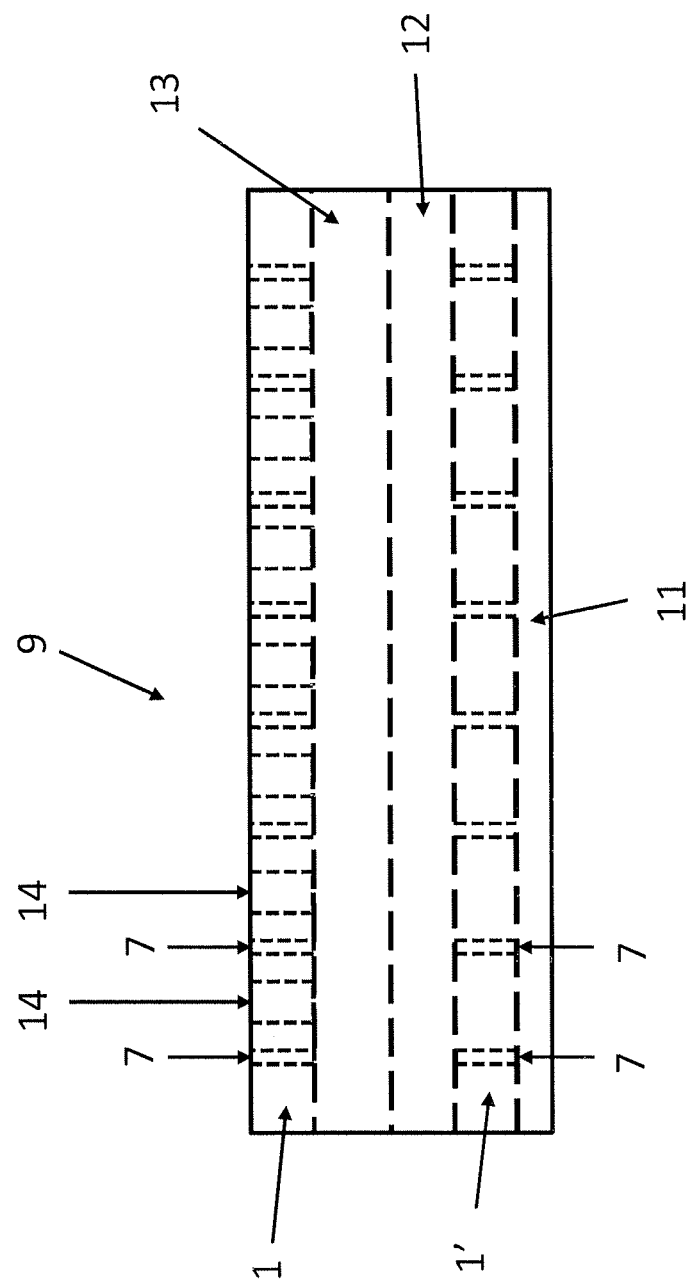
FIG. 12 schematically shows a side view of an absorbent article including a signal layer according to a twelfth embodiment.

FIG. 12 schematically shows a side view of an absorbent article 9 including a signal layer 1 according to a twelfth embodiment. FIG. 12 shows a similar absorbent article 9 to the one shown in FIG. 11 but with the difference that the first signal layer 1 makes up the upper layer 10 of the absorbent article 9.

Figure 13:
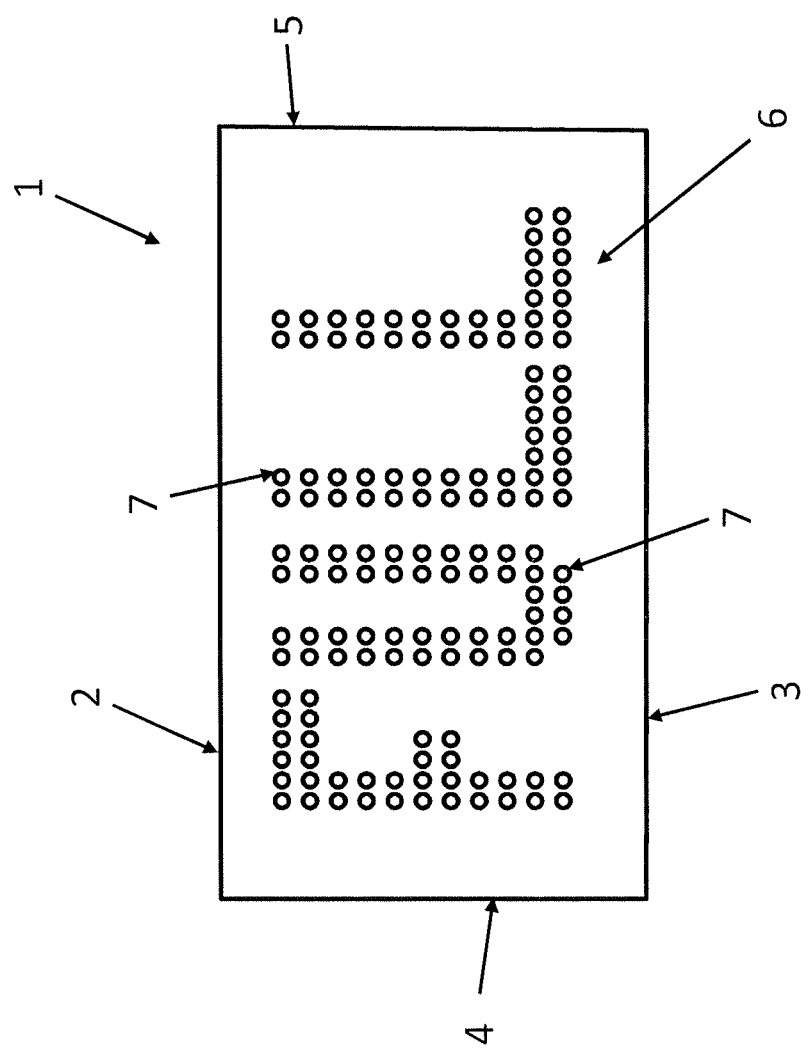
FIG. 13 schematically shows a signal layer according to a thirteenth embodiment.

FIG. 13 schematically shows a signal layer 1 according to a thirteenth embodiment. Here, one example of a pattern 6 is shown that illustrates a graphic message, in this instance the word "full". Other suitable words that can be formed using the capillary channels 7 are of course also conceivable such as "used", "full", "change", "Try a liner" or similar. The letters may be upper-case or lower-case or a combination thereof.

In the above FIGS. 4, 5, 9, 11 and 12, the capillary channels 7 have the same length as the through openings 14. This is for clarity only. As indicated above the capillary channels 7 have a length that is shorter than the length of the through openings 14 in order to reduce the contact between the capillary channels 7 and any of the underlying layers in order for liquid not to be drained from the capillary channels into an underlying layer.

Figure 14:
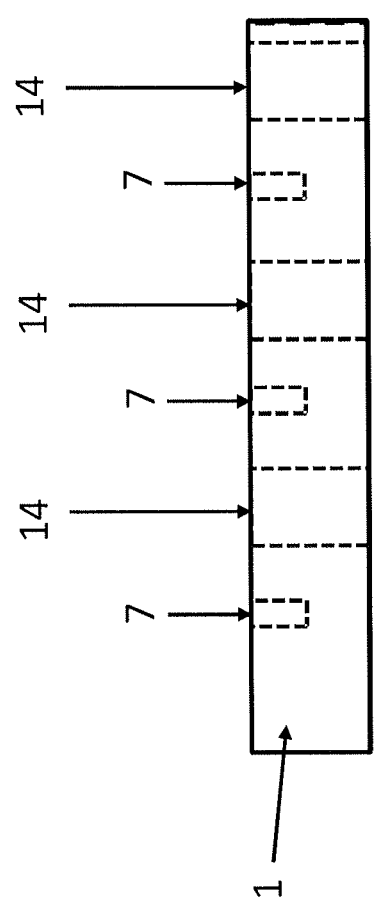
FIG. 14 schematically shows a detailed view of a signal layer including through openings.

FIG. 14 shows a detailed view of a signal layer 1 including both capillary channels 7 and through openings 14 to show an example of a relation between the capillary channels and the through openings. The relation illustrated in FIG. 14 is a mere example. The relation can be varied depending on what kind of layer is located beneath the capillary channels. In some cases, the capillary channels and the through openings may have the same length as indicated in FIGS. 4, 5, 9, 11 and 12. In order to avoid draining of liquid of the capillary channels by the material in the signal layer, the material in the signal layer has to be chosen such that no draining of the capillary channels takes place even though the capillary channels 7 are in contact with the material in the signal layer 1. This means that the material in the signal layer 1 is such that the capillary force in the underlying material is smaller than the capillary force in the capillary channels 7. The liquid retained in the capillary channels 7 thus stays in place as the capillary force of the capillary channels exceeds the capillary force of the underlying material.

Figure 15:
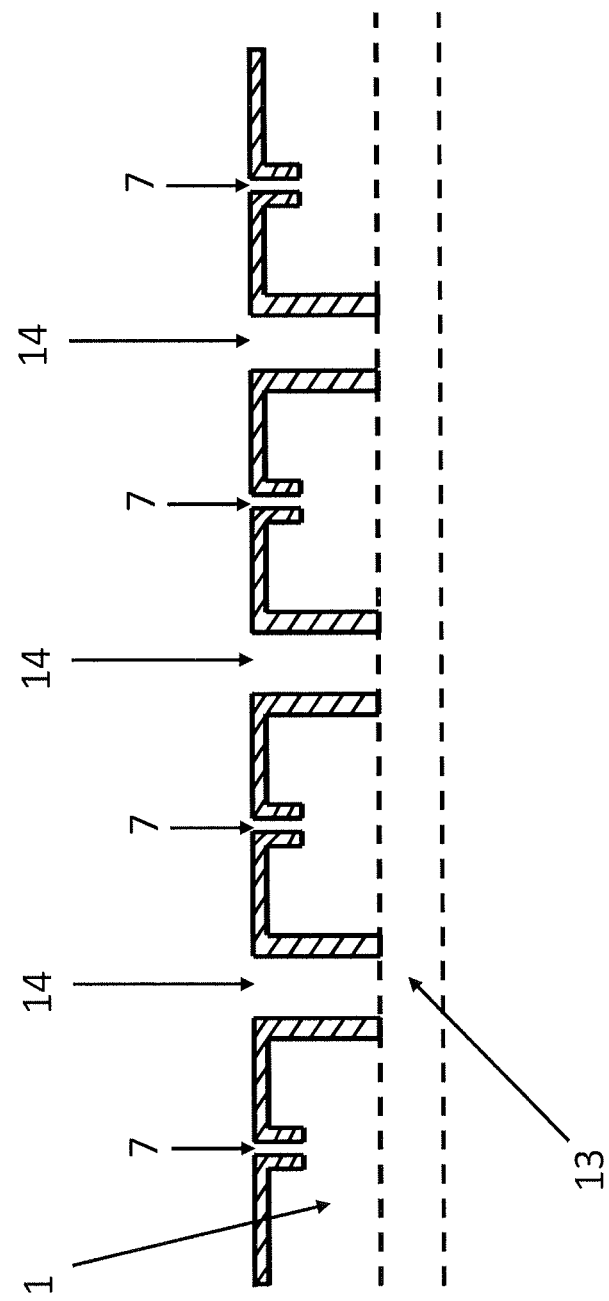
FIG. 15 schematically shows a detailed view of a signal layer including through openings.

FIG. 15 schematically shows a detailed view of a signal layer 1 including through openings 14. In FIG. 15, a cross section along the longitudinal centre line 8 in FIG. 8 is shown. For simplicity a view of alternating capillary channels 7 and through openings 14 are shown. As can be seen from FIG. 15, the through openings of signal layer 1 rests on an underlying layer, in this case illustrated by a distribution layer 13. Another possibility is that the through openings 14 act as distancing elements creating a space between the shorter capillary channels and the underlying layer. This means that there is no material between the capillary channels 7 and the distribution layer 13. Thus no draining of liquid retained in the capillary channels is possible by the underlying material. Other kinds of underlying layers described above are possible.

The configurations in FIGS. 14 and 15 may be used together with any of the absorbent articles or configurations of signal layers described in conjunction with FIGS. 1-13.

Further, one or more of the different configurations of signal layers and/or absorbent articles may be combined.

Reference signs mentioned in the claims should not be seen as limiting the extent of the matter protected by the claims, and their sole function is to make claims easier to understand.

As will be realised, the invention is capable of modification in various obvious respects, all without departing from the scope of the appended claims. Accordingly, the drawings and the description thereto are to be regarded as illustrative in nature, and not restrictive.

The invention claimed is:

1. An absorbent article having two opposing and longitudinally extending longitudinal side edges and two opposing and laterally extending lateral side edges, the absorbent article comprising:
    an upper layer;
    a back sheet opposing the upper layer, wherein the upper layer is directly attached to the back sheet at least along the side edges; and
    a signal layer comprising a pattern of capillary channels allowing capillary action such that discharged menstrual fluid that comes across one of the openings in the capillary channels enters into the capillary channels and is retained therein due to the capillary force, the signal layer comprised of a material with a capillary force smaller than a capillary force of the capillary channels,
    wherein the color of the retained menstrual discharge dyes or colors the pattern for a signaling purpose, and
    wherein the pattern is directly or indirectly visible to an observer.

2. The absorbent article according to claim 1, wherein the signal layer is positioned in the absorbent article such that it is visible through a back sheet in the absorbent article.

3. The absorbent article according to claim 1, wherein the signal layer is positioned in the absorbent article such that it is visible through an upper layer in the absorbent article.

4. The absorbent article according to claim 1, wherein the signal layer is at least one of a distribution layer or an acquisition layer of the absorbent article.

5. The absorbent article according to claim 1, wherein the upper layer comprises through openings that allow menstrual fluids to pass through the upper layer.

6. The absorbent article according to claim 5, wherein the through openings are slits, bent openings, angled through opening, or maze like through openings, for at least partly hindering menstrual fluids to be visible through the through openings.

7. The absorbent article according to claim 5, wherein the upper layer has a thickness equal to or larger than the extent of the through opening.

8. The absorbent article according to claim 1, wherein the signal layer comprises through openings that allow menstrual fluids to pass through the signal layer.

9. The absorbent article according to claim 8, wherein the signal layer has a thickness equal to or larger than the extent of the through opening.

10. The absorbent article according to claim 1, wherein the upper layer is a laminate comprising a non-woven bound to a substrate, wherein the non-woven is subtle to a user and translucent and/or transparent.

11. The absorbent article according to claim 1, wherein the signal layer is made from a perforated plastic film.

12. The absorbent article according to claim 1, wherein the signal layer is a laminate of several layers.

13. The absorbent article according to claim 1, wherein the capillary channels are positioned in a striking zone of the absorbent article.

14. The absorbent article according to claim 1, wherein the capillary channels are positioned in a barrier zone of the absorbent article for detection of a full article.

15. The absorbent article according to claim 1, wherein the signal layer is a laminate of several layers.

16. An absorbent article having two opposing and longitudinally extending longitudinal side edges and two opposing and laterally extending lateral side edges, the absorbent article comprising
    a signal layer comprising a pattern of capillary channels allowing capillary action such that discharged menstrual fluid that comes across one of the openings in the capillary channels enters into the capillary channels and is retained therein due to the capillary force, the signal layer comprised of a material with a capillary force smaller than a capillary force of the capillary channels; and
    a back sheet opposing the signal layer, wherein the signal layer is directly attached to the back sheet at least along the side edges,
    wherein the color of the retained menstrual discharge dyes or colors the pattern for a signaling purpose, and
    wherein the pattern is directly or indirectly visible to an observer.

17. The absorbent article according to claim 16, wherein the signal layer is a laminate comprising a non-woven bound to a substrate, wherein the non-woven is subtle to a user and translucent and/or transparent.

18. The absorbent article according to claim 16, wherein the signal layer comprises through openings that allow menstrual fluids to pass through the signal layer.

19. The absorbent article according to claim 18, wherein the through openings are slits, bent openings, angled through opening, or maze like through openings, for at least partly hindering menstrual fluids to be visible through the through openings.

20. The absorbent article according to claim 18, wherein the signal layer has a thickness equal to or larger than the extent of the through opening.

* * * * *